US006479046B2

(12) United States Patent
Dickens et al.

(10) Patent No.: US 6,479,046 B2
(45) Date of Patent: Nov. 12, 2002

(54) ATTRACTANTS AND REPELLANTS FOR COLORADO POTATO BEETLE

(76) Inventors: Joseph C. Dickens, 4430 Columbia Rd., Ellicott City, MD (US) 21042; A. Randall Alford, 23 Pond St., Orono, ME (US) 04473

( * ) Notice: Subject to any disclaimer, the term of this patent is extended or adjusted under 35 U.S.C. 154(b) by 0 days.

(21) Appl. No.: 09/925,131

(22) Filed: Aug. 9, 2001

(65) Prior Publication Data

US 2002/0076391 A1 Jun. 20, 2002

Related U.S. Application Data

(60) Provisional application No. 60/225,789, filed on Aug. 17, 2000.

(51) Int. Cl.[7] ......................... A01N 37/06; A01N 37/10; A01N 31/02; A01N 35/02; A01N 27/00
(52) U.S. Cl. ................................. 424/84; 424/DIG. 10; 514/544; 514/546; 514/693; 514/739; 514/766; 514/919
(58) Field of Search ........................... 424/84, DIG. 10; 514/544, 546, 693, 739, 766, 919

(56) References Cited

PUBLICATIONS

Dickens, Joseph C., "Orientation of Colorado Potato Beetle to Natural and Synthetic Blends . . . " Agricultural and Forest Entomology, vol. 2, No. 3, pp. 167–172, Aug. 2000.*
Schutz, S., et al., "Host Plant Selection of the Colorado Potato Beetle as Influenced by Damage Induced Volatiles of the Potato Plant", Naturwissenchaften, vol. 84, pp. 212–217, 1997.
Bolter, C.J., et al., "Attraction of Colorado Potato Beetle to Herbivore–Damaged Plants During Herbivory and After Its Termination", Journal of Chemical Ecology, vol. 23(4), pp. 1003–1023, 1997.
Levinson, H.Z., et al., "Sex Recognition by a Pheromone in the Colorado Beetle", Naturwissenchaften, vol. 66, pp. 472–473, 1979.
Jermy, T., et al., "Method for Screening Female Sex Pheromone Extracts of the Colorado Potato Beetle", Entomol. Exp. Appl., vol. 59, pp. 75–78, 1991.
Dickens, J.C., "Predator–Prey Interactions: Olfactory Adaptations of Generalist and Specialist Predators", Agricultural and Forest Entomology, vol. 1, pp. 47–54, 1999.
Pickett, J.A., et al., "Developing Sustainable Pest Control from Chemical Ecology", Agriculture, Ecosystems and Environment, vol. 64, pp. 149–156, 1997.
Carde, R.T., Chapter 4, "Principles of Mating Disruption", in Behavior–Modifying Chemicals for Insect Management: Applications of Pheromones and Other Attractants, edited by R. Ridgway et al., Marcel Dekker, Inc., Madison, NY, pp. 47–71, 1990.

Lainer, G.N., Chapter 3, "Principles of Attraction–Annihilation: Mass Trapping and Other Means", in Behavior–Modifying Chemicals for Insect Management: Applications of Pheromones and Other Attractants, edited by R. Ridgway et al., Marcel Dekker, Inc., Madison, NY, pp. 25–45, 1990.
Wall, C., Chapter 2, "Principles of Monitoring", in Behavior–Modifying Chemicals for Insect Management: Applications of Pheromones and Other Attractants, edited by R. Ridgway et al., Marcel Dekker, Inc., Madison, NY, pp. 9–23, 1990.
Michell, B.K., "The Chemosensory Basis of Host–Plant Recognition in Chrysomelidae", Novel Aspects of the Biology of Chrysomelidae, edited by P. Jolivet et al., pp. 141–151, 1994.
Ferro, D.N., et al., Chapter 12, "Management of Insect Pests", in Potato Health Management, edited by R. Rowe, pp. 103–116, 1993.
Otto, D., "Further Evidence for the Presence of a Female Sex Pheromone in the Colorado Potato Beetle Leptinotarsa decemlineata Say. and its Biological Characterization", Practice Oriented Results on Use and Production of Neem Ingredients and Pheromones IV, edited by H. Kleeberg et al., pp. 135–147, 1996.
Weissbecker, B., et al., "Analysis of Volatiles Emitted by Potato Plants by Means of a Colorado Beetle Electroantennographic Detector[1]", Talanta, vol. 44, pp. 2217–2224, 1997.

* cited by examiner

Primary Examiner—John Pak
(74) Attorney, Agent, or Firm—G Byron Stover; M. Howard Silverstein; John D. Fado

(57) ABSTRACT

A method has been discovered for attracting Colorado potato beetles to an area of object or area, which method involves treating the object or area with a Colorado potato beetle attracting composition (with or without an insecticide) containing a carrier material and a Colorado potato beetle attracting effective amount of (a) (Z)-3-hexenyl acetate, (±)-linalool, nonanal, and methyl salicylate, (b) (Z)-3-hexenyl acetate, (±)-linalool, and methyl salicylate, (c) (Z)-3-hexen-1-ol, (E)-2-hexen-1-ol, and (±)-linalool, (d) (Z)-3-hexenyl acetate and methyl salicylate, or (e) (Z)-3-hexenyl acetate and (±)-linalool. Furthermore, a method has been discovered for repelling Colorado potato beetles from an object or area, comprising treating the object or area with a Colorado potato beetle repelling composition (with or without an insecticide) containing a carrier material and a Colorado potato beetle repelling effective amount of (Z)-3-hexen-1-ol, (E)-2-hexen-1-ol, (±)-linalool, nonanal, methyl salicylate, and β-caryophyllene.

8 Claims, 6 Drawing Sheets

ATTRACTANTS AND REPELLANTS FOR COLORADO POTATO BEETLE

REFERENCE TO RELATED APPLICATION

This application claims the benefit of U.S. Provisional Application No. 60/225,789, filed Aug. 17, 2000, which is incorporated herein by reference in its entirety.

BACKGROUND OF THE INVENTION

The present invention relates to an attractant composition for Colorado potato beetles, which composition contains a carrier material and a Colorado potato beetle attracting effective amount of (a) (Z)-3-hexenyl acetate, (±)-linalool, nonanal, and methyl salicylate, (b) (Z)-3-hexenyl acetate, (±)-linalool, and methyl salicylate, (c) (Z)-3-hexen-1-ol, (E)-2-hexen-1-ol, and (±)-linalool, (d) (Z)-3-hexenyl acetate and methyl salicylate, or (e) (Z)-3-hexenyl acetate and (±)-linalool. The present invention also relates to a method for attracting Colorado potato beetles to an area of object or area, which method involves treating the object or area with a Colorado potato beetle attracting composition which contains a carrier material and a Colorado potato beetle attracting effective amount of (a) (Z)-3-hexenyl acetate, (±)-linalool, nonanal, and methyl salicylate, (b) (Z)-3-hexenyl acetate, (±)-linalool, and methyl salicylate, and wherein said beetles are larvae or adults, (c) (Z)-3-hexen-1-ol, (E)-2-hexen-1-ol, and (±)-linalool, (d) (Z)-3hexenyl acetate and methyl salicylate, or (e) (Z)-3-hexenyl acetate and (±)-linalool.

In addition, the present invention also relates to a composition for repelling Colorado potato beetles, which composition contains a carrier material and a Colorado potato beetle repelling effective amount of (Z)-3-hexen-1-ol, (E)-2-hexen-1-ol, (±)-linalool, nonanal, methyl salicylate, and β-caryophyllene. Furthermore, the present invention also relates to a method for repelling Colorado potato beetles from an object or area, which method involves treating the object or area with a Colorado potato beetle repelling composition which contains a carrier material and a Colorado potato beetle repelling effective amount of (Z)-3-hexen-1-ol, (E)-2-hexen-1-ol, (±)-linalool, nonanal, methyl salicylate, and β-caryophyllene.

The Colorado potato beetle (CPB), *Leptinotarsa decemlineata* (Say) (Coleoptera: Chrysomelidae), is one of the most damaging insect pests of potatoes (*Solanum tuberosum* L.). Since it was first noted as a pest of potatoes in 1859, CPB has developed resistance to numerous chemicals that have been applied for its control (Casagrande, R. A., Bulletin of the Entomological Society of America, 142–150 (1987)). Alternatives to pesticides, e.g., biocontrol agents and host plant resistance, have had promising results and may enhance programs aimed at integrated pest management. Behavioral chemicals such as pheromones and plant attractants could also be useful both in survey and control of CPB (Dickens, J. C., Agricultural and Forest Entomology, 1: 47–54 (1999)).

Orientation of CPB to conspecifics and its host plant has been investigated intensively during this century. Although several studies have demonstrated the presence of a contact pheromone involved in CPB mating on the elytra of females (Jermy, T., et al., Entomologia Experimentalis et Applicata, 59: 75–78 (1991); Otto, D., Further evidence for the presence of a female sex pheromone in the Colorado potato beetle *Leptinotarsa decemlineata* Say. and its biological characterization, pp. 135–147, in H. Kleeberg and V. Micheletti (eds.), Practice Oriented Results on Use and Production of Neem Ingredients and Pheromones IV, Trifolio-M GmbH (1996)), proof of a sex pheromone that is active over a distance has been more elusive (DeWilde, J., et al., Netherlands Journal of Plant Pathology, 75: 53–57 (1969); Levinson, H. Z., et al., Naturwissenschaften, 66: 472–473 (1979); Edwards, M. A., et al., The Canadian Entomologist, 129: 667–672 (1997)). An olfactometer was devised that showed the attractiveness of volatiles emitted by potato plants to CPB adults (Mclndoo, N. E., Journal of Economic Entomology, 19: 545–571 (1926)); the first demonstration that volatile emissions by plants attract insects. While various other investigators verified Mclndoo's initial observation (Schanz, M., Zeitschrift fir vergleichende Physiologie, 35: 353–379 (1953); De Wilde, J., et al., Netherlands Journal of Plant Pathology, 75: 53–57 (1969); Visser, J. H., Entomologia Experimentalis et Applicata, 20: 275–288 (1976); Bolter, C. J., et al., Journal of Chemical Ecology, 23: 1003–1023 (1997)), specific chemical blends of plant odors responsible for attraction of CPB to potato plants have remained a mystery.

Volatiles emitted by intact potato plants, plants that were mechanically-damaged or plants that were damaged by insect feeding were identified in two separate studies (Bolter, C. J., et al., Journal of Chemical Ecology, 23: 1003–1023 (1997); Schütz, S., et al., Naturwissenschaften, 84: 212–217 (1997)). Bolter et al. (1997) revealed that feeding by CPB larvae on potato plants (cultivar Surprise) results in emission of a number of compounds including the green leaf volatile derivatives, (Z)-3-hexenol and (Z)-3-hexenyl butyrate, and the sesquiterpenes, β-caryophyllene and β-selenine. Linalool and indole were among volatiles emitted by CPB-damaged plants 24 hours following removal of the insects (Bolter et al., 1997). In their study, the blend of volatile compounds released by intact plants was not "strikingly different" from the blend emitted by insect damaged plants, and while a higher level of attraction of CPB was observed to insect-or mechanically-damaged plants, intact plants were also attractive. Schütz et al. (1997) used coupled gas chromatography/electroantennographic detector recordings to show that CPB antennae detect at least 18 compounds released by damaged potato plants (cultivar Granola). Benzene methanol and 2-benzene-ethanol were emitted by beetle-damaged plants but were not released by mechanically-damaged plants. Leaves sprayed with paraffin solutions of linalool, benzene methanol, 2-benzene-ethanol, or β-caryophyllene were attractive to CPB, while β-myrcene, nonanal and (Z)-3-nonen- 1-ol applied in a similar manner reduced attraction.

Recently, there was disclosed a novel technique in which electroantennograms (EAGs) were recorded from CPB antennae that were challenged with equal amounts of compounds released by potato plants (an "isosynthetic potato plant") delivered by gas chromatography (Dickens, J. C., Agricultural and Forest Entomology, 1: 47–54 (1999)). Employing serial dilutions to determine near threshold responses, these recordings showed that CPB, a generalist predator (*Podisus maculiventris*(Say) Hemiptera, Heteroptera: Pentatomidae), and a specialist predator (*Perillus bioculatus*(F.) Hemiptera, Heteroptera: Pentatomidae) of CPB possessed antennal olfactory receptors that were selectively sensitive to potato volatiles. Behavioral bioassays revealed that the generalist predator was attracted to a five-component volatile blend comprised of (E)-2-hexen-1-ol, (Z)-3-hexen-1-ol, nonanal, (±)-linalool, and methyl salicylate. CPB were attracted to a similar five-component blend in which the relative amounts of (E)-2-hexen-1-ol and (Z)-3-hexen-1-ol were decreased. This was the first synthetic attractant known for CPB. With the exception of (E)-2-hexen-1-ol for which CPB were more sensitive, antennal receptors of CPB were less sensitive to components of the blend than were both the generalist and specialist predators. Since green leaf volatiles (e.g., (E)-2-hexen-1-ol) are emitted at CPB feeding sites, it was hypothesized that such compounds might facilitate spacing of CPB on the plant, thereby improving its utilization by the insect.

In the present study, the behavior of CPB to natural and synthetic blends of volatiles emitted by potato plants was investigated.

SUMMARY OF THE INVENTION

In accordance with the present invention there is provided an attractant composition for Colorado potato beetles, which composition contains a carrier material and a Colorado potato beetle attracting effective amount of (a) (Z)-3-hexenyl acetate, (±)-linalool, nonanal, and methyl salicylate, (b) (Z)-3-hexenyl acetate, (±)-linalool, and methyl salicylate, (c) (Z)-3-hexen-1-ol, (E)-2-hexen-1-ol, and (±)-linalool, (d) (Z)-3-hexenyl acetate and methyl salicylate, or (e) (Z)-3-hexenyl acetate and (±)-linalool.

Also in accordance with the present invention is a method for attracting Colorado potato beetles to an area of object or area, which method involves treating the object or area with a Colorado potato beetle attracting composition which contains a carrier material and a Colorado potato beetle attracting effective amount of (a) (Z)-3-hexenyl acetate, (±)-linalool, nonanal, and methyl salicylate, (b) (Z)-3-hexenyl acetate, (±)-linalool, and methyl salicylate, and wherein said beetles are larvae or adults, (c) (Z)-3-hexen-1-ol, (E)-2-hexen- 1-ol, and (±)-linalool, (d) (Z)-3-hexenyl acetate and methyl salicylate, or (e) (Z)-3-hexenyl acetate and (±)-linalool.

In addition, there is also provided a composition for repelling Colorado potato beetles, consisting essentially of a carrier material and a Colorado potato beetle repelling effective amount of (Z)-3-hexen-1-ol, (E)-2-hexen-1-ol, (±)-linalool, nonanal, methyl salicylate, and β-caryophyllene.

Furthermore, there is also provided a method for repelling Colorado potato beetles from an object or area, comprising treating the object or area with a Colorado potato beetle repelling composition consisting essentially of a carrier material and a Colorado potato beetle repelling effective amount of (Z)-3-hexen-1-ol, (E)-2-hexen-1-ol, (±)-linalool, nonanal, methyl salicylate, and β-caryophyllene.

DETAILED DESCRIPTION OF THE INVENTION

Figure 1A:
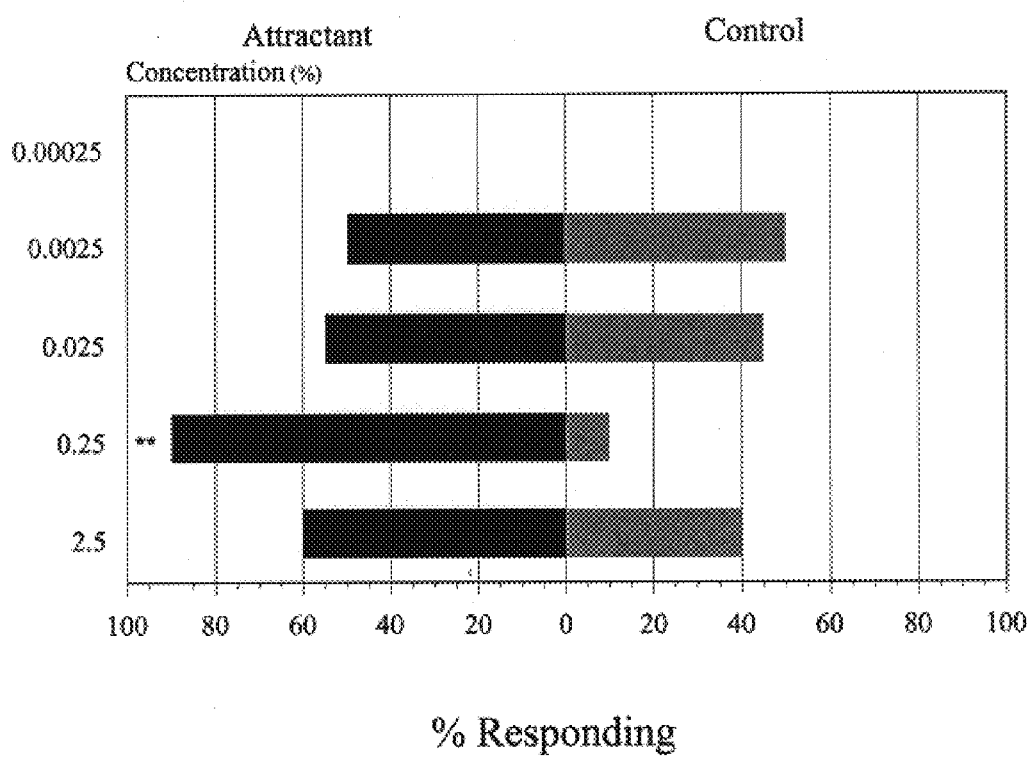
FIG. 1a shows a dose response bioassay for second instar larvae to a synthetic blend (a three component blend containing (Z)-3-hexenyl acetate, (±)-linalool and methyl salicylate)
Figure 1B:
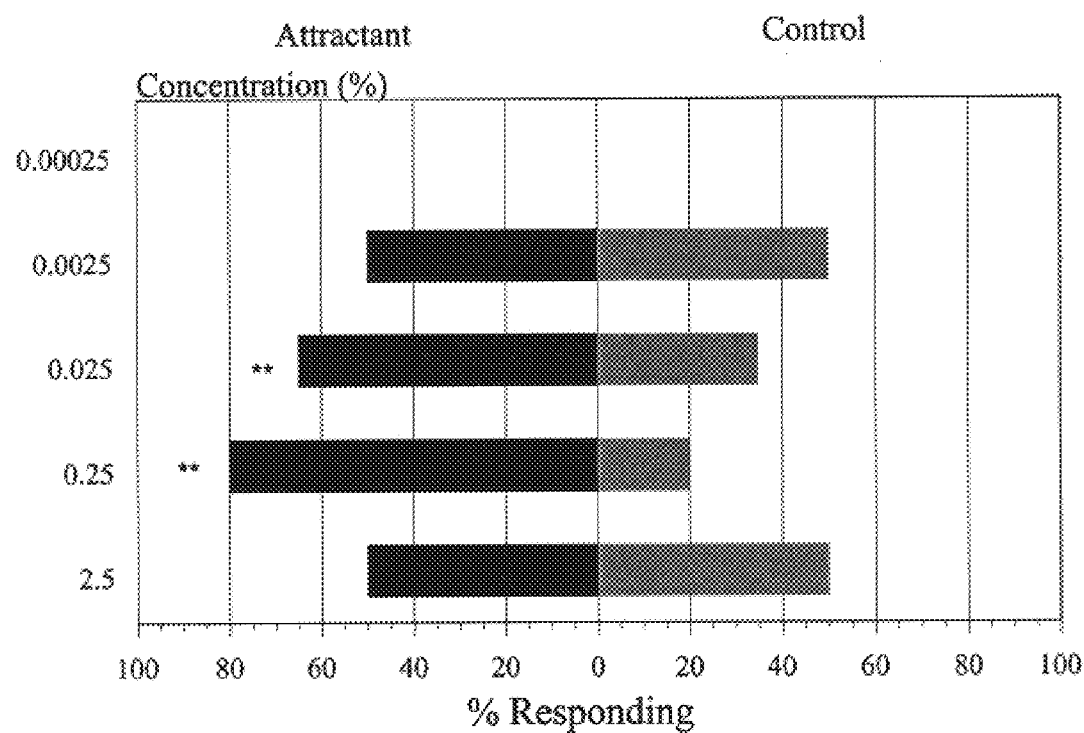
FIG. 1b shows a dose response bioassay for fourth instar larvae to the synthetic blend.
Figure 1C:
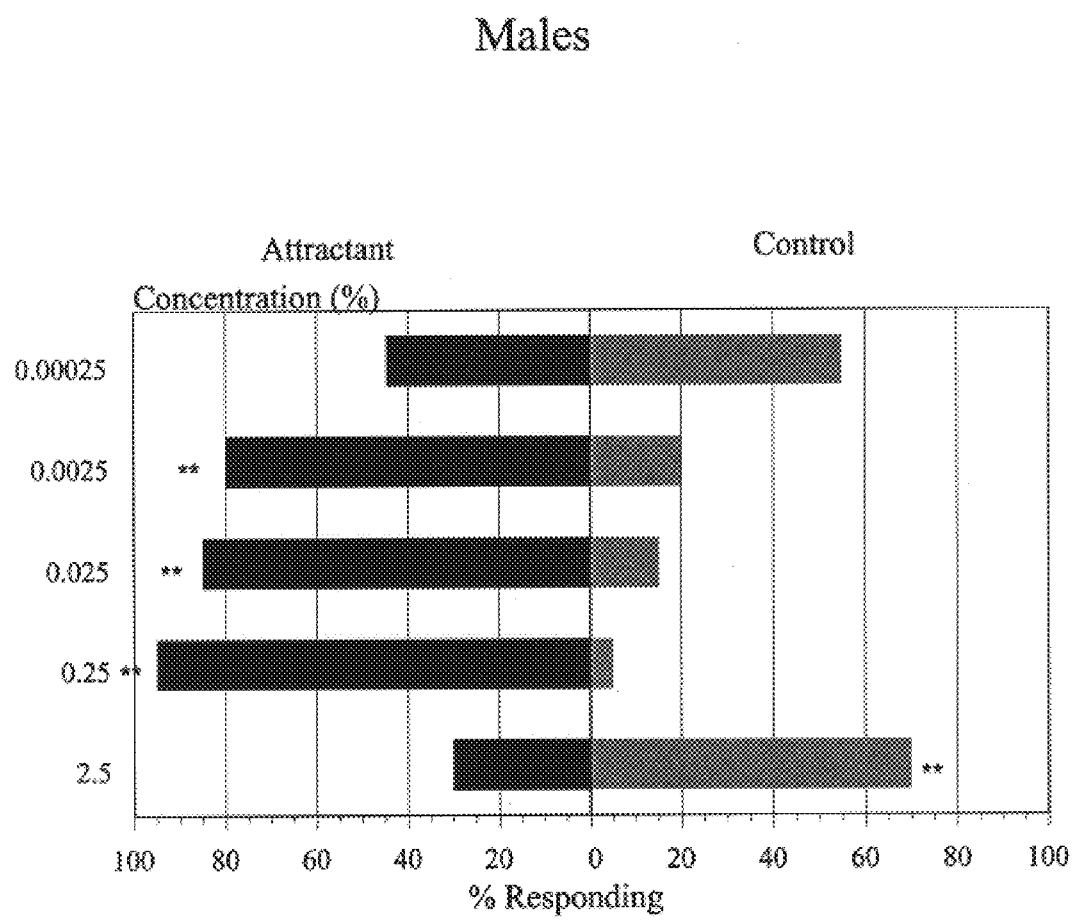
FIG. 1c shows a dose response bioassay for adult males to the synthetic blend.
Figure 1D:
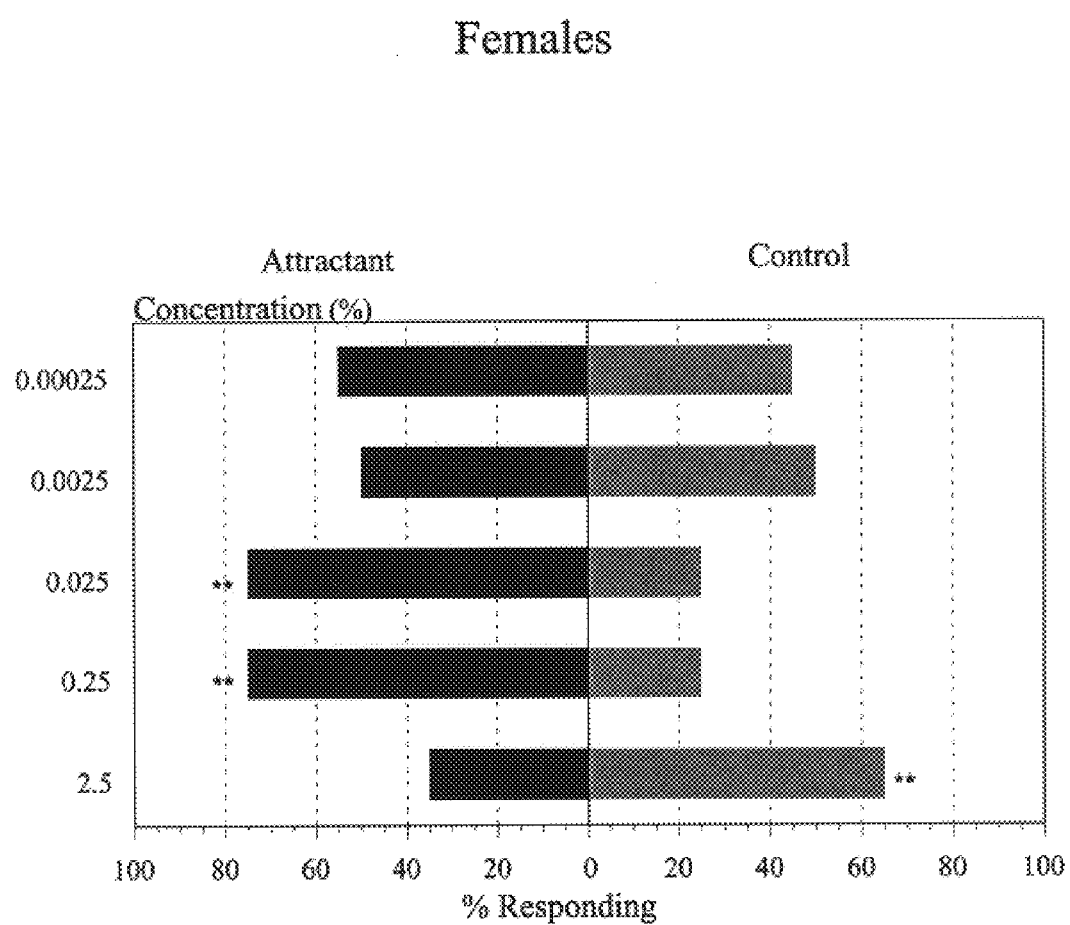
FIG. 1d shows a dose response bioassay for adult females to the synthetic blend.

A method is disclosed for attracting Colorado potato beetles to an object or area, comprising treating the object or area with a Colorado potato beetle attracting composition comprising a carrier material and a Colorado potato beetle attracting effective amount of (a) (Z)-3-hexenyl acetate, (±)-linalool, nonanal, and methyl salicylate, (b) (Z)-3-hexenyl acetate, (±)-linalool, and methyl salicylate, and wherein said beetles are larvae or adults, (c) (Z)-3-hexen-1-ol, (E)-2-hexen-1-ol, and (±)-linalool, (d) (Z)-3-hexenyl acetate and methyl salicylate, or (e) (Z)-3-hexenyl acetate and (±)-linalool.

Also disclosed is a method for repelling Colorado potato beetles from an object or area, comprising treating the object or area with a Colorado potato beetle repelling composition consisting essentially of a carrier material and a Colorado potato beetle repelling effective amount of (Z)-3-hexen-1-ol, (E)-2-hexen-1-ol, (±)-linalool, nonanal, methyl salicylate, and β-caryophyllene.

The attractant or repellant of the present invention is applied with a carrier component. The carrier component can be a liquid or a solid material. As is known in the art, the vehicle or carrier to be used refers to a substrate such as a membrane, hollow fiber, microcapsule, cigarette filter, gel, polymers, or the like. All of these substrates have been used to release insect attractants and repellants and are well known in the art.

The amount of attractant used will be at least an effective amount. The term "effective amount," as used herein, means the minimum amount of attractant needed to attract the Colorado potato beetle to a treated area or object when compared to the same area or object which is untreated. Effective concentrations of the attractant blends in the compositions may vary between 0.0025% to about 20%. Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedure utilized in Table 3 below; the attractant would attract more than 50% of the beetles and would be statistically significant in comparison to a control. The attractant composition may or may not contain a control agent for Colorado potato beetles, such as a biological control agent or an insecticide known in the art to kill Colorado potato beetles. Other compounds may be added to the attractant composition provided they do not substantially interfere with the intended activity of the attractant composition; whether or not a compound interferes with attractant activity can be determined, for example, by the procedure utilized in Table 3.

The attractants could be used in pest management strategies(1) as a component of an attracticide which combines it with a feeding stimulant and lethal doses of insecticide or pathogen. Such an attracticide would not only specifically target CPB populations but would also result in an overall decrease in application rates for pesticides to potato crop ecosystems; (2) for monitoring populations of colonizing adult beetles early in the season; (3) in deployment of the trap crop method of CPB control; (4) to indicate CPB movement within potato fields; or (5) in conjunction with antifeedants (Murray, K. D., et al., Entomol. Exp.

Appl., 80: 503–510 (1996)) in "push-pull" strategies of insect management.

The amount of repellant used will be at least an effective amount. The term "effective amount," as used herein, means the minimum amount of repellant needed to repel the Colorado potato beetle to a treated area or object when compared to the same area or object which is untreated. Effective concentrations of the repellant blends in the compositions may vary between 0.0025% to about 20%. Of course, the precise amount needed will vary in accordance with the particular repellant composition used; the type of area or object to be treated; the number of days of repelling needed; and the environment in which the area or object is located. The precise amount of repellant can easily be determined by one skilled in the art given the teaching of this application. For example, one skilled in the art could follow the procedure utilized in Table 3 below; the repellant would repel more than 50% of the beetles and would be statistically significant in comparison to a control. The repellant composition may or may not contain a control agent for Colorado potato beetles, such as a biological control agent or an insecticide known in the art to kill Colorado potato beetles. Other compounds may be added to the repellant composition provided they do not substantially interfere with the intended activity of the repellant composition; whether or not a compound interferes with repellant activity can be determined, for example, by the procedure utilized in Table 3.

Those blends shown to be repellent to CPB could be used in pest management strategies: (1) in conjunction with the attractant or trap crops in "push-pull" strategies of insect management; (2) either alone or in combination with nonvolatile feeding deterrents to protect the potato crop. Additionally, increased knowledge of chemical signals used by CPB could be important in genetic engineering of crops with differing levels of attractiveness.

The following examples are intended only to further illustrate the invention and are not intended to limit the scope of the invention as defined by the claims

EXAMPLE I

Insects: Adult Colorado potato beetles (CPB) were obtained from a laboratory colony which was annually infused with feral insects. CPB were maintained on potato, *S. tuberosum* cultivar Kennebeck, for both larval and adult stages. Upon emergence, adults were sexed; individual insects were kept in plastic containers with fresh potato foliage and water until use six to 12 days post emergence. Prior to testing, CPB were starved for two to three hours. Experimental insects were used only once.

Odorous stimuli: The source and purity of the chemicals used in this study are listed in Table 1. Odorous blends tested are described in Table 3.

Plant stimuli consisted of 4.8 g of leaves from mature plants that were mechanically-damaged using scissors to make incisions ca. 1 cm in length at ca. 1 cm intervals around the circumference of leaves. Foliage used in the study were, potato, *S. tuberosum* cultivar Kennebeck (Solanaceae); tomato, *Lycopersicon esculentum* Mill cultivar Pik Red (Solanaceae); and soybean, *Glycines max* cultivar Williams (Leguminaceae).

Experimental protocol: Chemical blends and plant foliage were tested for behavioral activity in an open Y-track olfactometer modified after Visser et al. (Visser, J. H., et al., Proceedings of the Section Experimental and Applied Entomology of the Netherlands Entomological Society Amsterdam, 9: 41–46 (1998); and described in detail by Dickens (Dickens, J. C., Agricultural and Forest Entomology, 1: 47–54 (1999)). In brief, odorous stimuli emanating from synthetic blends on filter paper discs (2.5 cm dia., Whatman™ #1 filter paper) or mechanically-damaged plant foliage in Ehrlenmeyer flasks were delivered to either side of the device. For each blend, a total amount of 25 $\mu$l of neat chemicals were diluted in 1 ml of mineral oil (25 $\mu$g total chemicals/$\mu$l mineral oil). For example, 8.33 $\mu$l of each compound was needed for a 3 component blend, while 5 $\mu$l of each compound was needed for a 5 component blend. A 10× dilution (2.5 $\mu$g total chemicals/$\mu$l mineral oil) of the appropriate blend was prepared for use in the bioassay where 25 $\mu$l of the blend was applied to the filter paper disk placed in the Ehrlenmeyer flask; 25 $\mu$l of paraffin oil served as the solvent control. "Low" in Table 3 refers to blends in which the designated compounds were ten times less than in related blends (e.g. (Z)-3-hexen-1-ol and (E)-2-hexen-1-ol are ten times less in blend II than in blend I). Hydrocarbon free air that was humidified by passing through distilled water carried the odor molecules to either arm of the bioassay apparatus. Treatments, both foliage and synthetic chemical blends, were replenished after 30 min of use in the bioassay apparatus. Airflow was regulated to 1 liter/min by flowmeters. Experiments were conducted in a darkened room at 22° C., in which the only source of light was that associated with the bioassay device. For all bioassays, at least 20 males and 20 females were tested.

Statistical analysesLaboratory bioassays were assessed for significant differences by the hypothesis on binomial proportions based on the standard normal approximation (Brase, C. H., et al., Understanding Statistics, D. C. Heath and Co., Lexington, Mass., XIV +489 pp. (1983)).

Results

Response to mechanically-damaged plants: CPB were significantly attracted to mechanically-damaged potato foliage (P<0.05), while response to tomato foliage was not significant (Table 2). When offered a choice between potato and tomato foliage, both solanaceous plants, preference of CPB for potato lacked significance. In contrast, CPB preferred potato foliage to foliage of soybean, a non-solanaceous plant (P<0.01).

Response to synthetic blends and individual chemicals: Of sixteen volatile treatments tested, CPB preferred 6 blends, avoided 2 blends, or showed no significant preference for 5 blends and 3 individual chemicals for the treatment versus the control (Table 3). Blends I, II, and III, each containing the green leaf volatiles, (Z)-3-hexen-1-ol and (E)-2-hexen-1-ol, and the sesquiterpene, β-caryophyllene, were unattractive. In fact, CPB avoided blends I and II with relatively higher amounts of β-caryophyllene (P<0.01); blend III with lower amounts of the green leaf volatiles and β-caryophyllene was also unattractive. Blends with the higher levels of green leaf volatiles, (Z)-3-hexen-1-ol and (E)-2-hexen-1-ol, were unattractive with (IV) or without (V) (Z)-3-hexenyl acetate.

Attractive blends all contained either low amounts of the green leaf volatiles, (E)-2-hexen-1-ol and (Z)-3-hexen-1-ol, or (Z)-3-hexenyl acetate, combined with (±)-linalool, nonanal, and/or methyl salicylate (Table 3: VI, VII, VIII, X, XI and XII); "low" amounts in Table 3 means that (E)-2-hexen-1-ol and (Z)-3-hexen-1-ol were present in the blend at 10% of the concentration of the other compounds in the blend (in general, "low" amounts means that the compounds in question can be present at 1–50% of the concentration of the other compounds in the blend, preferably at 10%). The four component blend of (Z)-3-hexenyl acetate, (±)-linalool, nonanal and methyl salicylate (VII) was equally as attractive as a similar five component blend containing low amounts of (E)-2-hexen-1-ol and (Z)-3-hexen-1-ol with (±)-linalool, nonanal and methyl salicylate (VI). Omission of nonanal from the four component blend (VII) revealed a sexually dimorphic response to the resulting three component blend (VIII) comprised of (Z)-3-hexenyl acetate, (±)-linalool and methyl salicylate; however in subsequent tests, this three component blend attracted both males and females (males: 140 to treatment, 16 to control; females, 113 to treatment, 23 to control). When (Z)-3-hexenyl acetate was omitted from the four component blend (VII), the resulting three component blend (IX) was unattractive.

Two component blends comprised of (Z)-3-hexenyl acetate in combination with either methyl salicylate (XI) or (±)-linalool (XII) were significantly attractive to both male and female CPB (P<0.01). Low amounts of (Z)-3-hexen-1-ol and (E)-2-hexen-1-ol could be substituted for (Z) 3-hexenyl acetate (see XII) in combination with (±)-linalool without loss of attraction (X). The combination of (±)-linalool and methyl salicylate was unattractive (XIII), as were (Z)-3-hexenyl acetate (XIV), (+)-linalool (XV) and methyl salicylate (XVI) tested individually.

Neither of two attractive blends, VI and VII, placed in competition with each other was preferred (Table 4). Similarly, there was no significant difference in preference of CPB for either VI or VII in competition with mechanically-damaged potato foliage.

Response of CPB larvae to synthetic blends: Of six volatile treatments tested that were attractive to adult CPB, CPB larvae (fourth instars in Table 5 and second instars in Table 6)) showed significant preference for only 1 blend, VIII ,which is a three component blend comprised of (Z)-3-hexenyl acetate, (±)-linalool and methyl salicylate. Dose response bioassays were also performed in the laboratory for two larval instars (second and fourth instars; CPB have four instars before becoming an adult) and both male and female adults (FIG. 1). In FIG. 1, bars with "**" along side them indicate that the response is statistically significant. The "concentration (%)" indicates the percent of the attractant solution which was comprised of the attractant blend VIII. Each bar represents responses of at least 20 insects.

Discussion: CPB prefer the odor of mechanically-damaged potato foliage to that of a control, while tomato foliage is not preferred in a similar situation (Table 2). Offered a choice between odor emanating from the two solanaceous plants, tomato and potato, neither is preferred. The attractiveness of potato odor to CPB has been previously reported (McIndoo, N. E., Journal of Economic Entomology, 19: 545–571 !1926)); Schanz, M., Der Geruchssinn des Kartoffelkäfers (*Leptinotarsa decemlineata* Say), Zeitschrift für vergleichende Physiologie, 35: 353–379 (1953)); DeWilde, J., Symposium Biology Hungary, 16: 291–300 (1976); Visser, J. H., et al., Entomologia Experimentalis et Applicata, 24: 538–549 (1978)). McIndoo (1926) showed attractive responses of CPB to both undamaged potato, and, to a lesser level, tomato plants (although statistical analyses were not employed). Visser and Nielsen (Entomologia Experimentalis et Applicata, 21: 14–22 (1977)) observed that positive anemotaxis of newly emerged female CPB was enhanced by volatiles emanating from undamaged solanaceous plants including potato and tomato, *S. lycopersicum*. Bolter et al. (Bolter, C. J., et al., Journal of Chemical Ecology, 23: 1003–1023 (1997)) noted that the attractiveness of undamaged potato plants was enhanced by both mechanical wounding and feeding by either CPB larvae or larvae of the beet armyworm, *Spodoptera exigua* Hübner (Lepidoptera: Noctuidae). Attraction of CPB to potato foliage over soybean foliage observed in the present study demonstrates preference of CPB for its solanaceous host plant over a non-solanaceous plant (Table 2). Previously, non-solanaceous plants either were attractive when in competition with a control (McIndoo, 1926), or enhanced, reduced, or had little effect on upwind anemotaxis (DeWilde, J., Symposium Biology Hungary, 16: 291–300 (1976)); DeWilde, J., et al., Netherlands Journal of Plant Pathology, 75: 53–57 (1969)); Thiery, D., et al., Journal of Chemical Ecology, 13: 1139–1146 (1987)).

Two chemical blends avoided by CPB contained green leaf volatiles (GLVs), (Z)-3-hexen-1-ol and (E)-2-hexen-1-ol, and the sesquiterpene, β-caryophyllene (Table 3 blends I and II). While all three compounds may be released in small amounts by undamaged potato plants (depending on the potato cultivar), emission levels for all are greatly increased either by mechanical damage or feeding by CPB larvae (Bolter et al., 1997; Schütz, S., et al., Naturwissenschaften, 84: 212–217 (1997)). Sensitivity of CPB to GLVs has been reported (Ma, W.C., et al., Entomologia Experimentalis et Applicata, 24: 320–333 (1978); Visser (1979)), and GLVs may modify behavioral responses of CPB to volatiles emitted by potato plants (Visser and Avé, 1978). Recently, it was shown that CPB preferred a five component blend containing these two GLVs, while a similar blend with increased levels of GLVs was unattractive to CPB but was attractive to a predator, *Podisus maculiventris* Say (Heteroptera, Hemiptera: Pentatomidae)(Dickens, 1999). Since high levels of GLVs are emitted constitutively at the feeding site, these high concentrations could facilitate spacing of CPB on the plant, and perhaps guide predators to their prey. Copious increases in levels of β-caryophyllene emitted from potato plants following feeding or mechanical damage could also signal predators or parasitoids of potential prey and may disperse CPB on the plant based on the effects of β-caryophyllene observed in my current study.

Minimal blends necessary for CPB attraction were comprised of (Z)-3-hexenyl acetate, (±)-linalool, and methyl salicylate. Two component blends of these chemicals were attractive so long as (Z)-3-hexenyl acetate was one of the components. Low levels of (Z)-3-hexen-1-ol and (E)-2-hexen-1-ol substitute for (Z)-3-hexenyl acetate when in combination with (±)-linalool. (Z)-3hexenyl acetate and methyl salicylate increase to detectable levels in potato (*S. tuberosum* cultivar Surprise) 20 hours following CPB infestation; linalool, already detectable from intact plants, increases dramatically after only 2 hours of CPB infestation (Bolter et al., 1997). Release by the plant of volatile blends containing these compounds could signal CPB feeding and may guide conspecifics to suitable host plants for feeding, mating or oviposition.

In summary, CPB are attracted by volatiles emitted by mechanically-damaged potato plants. Its solanaceous host plant, potato, is preferred over a non-solanaceous host, soybean, but in the present bioassay not over another solanaceous host, tomato. Synthetic blends of chemicals emitted by potato plants were attractive to CPB; one specific blend under the current experimental conditions elicited larval attraction. At least two synthetic blends were as attractive as mechanically-damaged potato foliage in the dual choice bioassay. Other than a single five component blend reported in an earlier study (Dickens, 1999), these are the first synthetic blends shown to be attractive to the CPB. These blends provide bases for manipulation of chemicallymediated behavior of CPB as a component of integrated pest management and are currently being tested in the field.

EXAMPLE II

Chemical lures: The chemical blend used in this study was selected based on its attractiveness to CPB in laboratory bioassays. The attractant blend was comprised of three components: (Z)-3-hexenyl acetate, 98% purity, obtained from Sigma, St. Louis, Mo. U.S.A.; (±)-linalool, 97% purity, and methyl salicylate, 99% purity, both obtained Aldrich, St. Louis, Mo. U.S.A. This blend was attractive to both adult and larval CPB in laboratory behavioral bioassays.

Cigarette filters (2.54 cm in length x0.7 cm diameter obtained from Filtrona Richmond Inc., Richmond, Va. U.S.A.) were used as release substrates for the experimental treatment which were diluted with: 20% polyethylene glycol; 42.5% methanol; 25% glycerol; 12.5% distilled water (Dickens, J. C., Entomol. Exp. Appl., 52: 191–203 (1989)). Blends of active components were mixed with the diluent at 1% level; 0.5 ml of the blend was injected with a syringe into the filters.

Traps: Pitfall traps used to capture beetles were comprised of 20.32 cm diameter green plastic pots that were placed in holes dug in the soil so the lip of the pot was flush with the ground level. A bar 0.61 m in length was driven into the soil at a depth of 15.2 cm to secure the pot and also to serve as a means to attach plastic foliage to simulate the potato canopy. The inside wall of each trap was covered with the adhesive, Tanglefoot™ (Tanglefoot, Grand Rapids, Mich., U.S.A.) to retain responding beetles.

Two lures (one placed at ground level, the other placed below ground level) for both attractant and control treatments were attached to the bar holding the foliage. To protect the lures from rain, each lure was held within one side of a 5.1 cm plastic Petri dish.

Field Plots: Studies were conducted in two fields (large field 0.404 Ha, small field 0.202 Ha) planted with potatoes, *Solanum tuberosum* var. Kennebec located at the University of Maine, Rogers Farm, Stillwater, Me. Studies began with emergence of the plants. A total of 42 traps were monitored: 22 traps were evenly spaced around the perimeter of the large field; 20 traps were evenly spaced around the perimeter of the small field. Attractant and control treatments were alternated spatially among the traps. Insects were collected from traps every other day between 1200H and 1400H. Due to environmental factors, beetles were not sexed following removal from traps.

Data Analyses. A t-test for unequal variances was used to compare attractant and control treatments (SAS).

Results: Traps baited with the three component blend of (Z)-3-hexenyl acetate, (±)-linalool and methyl salicylate captured 8 to 10 × as many Colorado potato beetle adults as control traps (Table 1). In the large field, traps baited with the attractant averaged 2.45 CPB per check compared to only 0.32 CPB in the controls. Similar results were found for the small field where the attractant-baited traps averaged 2.78 CPB per check compared with only 0.25 CPB in control traps. The number of CPB captured in attractant-baited traps were significantly different from control traps for both the large and small fields (P<0.01,t-test for unequal variances).

Table 1. Analyses (t-test: two-sample assuming unequal variances) of data obtained from tests in two potato fields (A. Large field, 0.75 acre; B. Small field, 0.5 acre) of attractant for Colorado potato beetle at Roger's Farm site in Orono, Me. The three component attractant comprised of (Z)-3-hexenyl acetate, (±)-linalool and methyl salicylate was compared to a control treatment (diluent only). The left column shows the results for the three component attractant and the right column shows the results for the control:

A. Large field, 0.75 acre

| Mean number CPB/trap | 2.45 | 0.32 |
|---|---|---|
| Variance | 7.05 | 0.37 |
| Observations | 66 | 66 |
| Hypothesized mean difference | 0 | |
| Degrees of freedom | 72 | |
| T statistic | 6.37** | |

B. Small field, 0.5 acre

| Mean number CPB/trap | 2.78 | 0.25 |
|---|---|---|
| Variance | 6.85 | .26 |
| Observations | 60 | 60 |
| Hypothesized mean difference | 0 | |
| Degrees of freedom | 63 | |
| T statistic | 7.36** | |

**-P < 0.01

Discussion: The results above demonstrate the attractiveness of this three component blend under field conditions. Preliminary results with other blends shown to be attractive in laboratory verified their attractiveness in field tests. Therefore, attractants of CPB may be useful in trap-out strategies for CPB control.

EXAMPLE III

Experimental treatments: The attractant blend was comprised of three components(Z)-3-hexenyl acetate, 98% purity, obtained from Sigma (St. Louis, Mo. U.S.A.); (±)-linalool, 97% purity, and methyl salicylate, 99% purity, both obtained from Aldrich (St. Louis, Mo. U.S.A.). This blend was attractive to both adult and larval CPB in laboratory behavioral bioassays. Two formulations of the three component volatile blend were prepared for field use by IPM Technologies, Inc. (Portland, Oreg. U.S.A.). First, the attractant blend was comprised of 10% of equal amounts by weight of the three components. Second, the attracticide was comprised of the same amount of the blend components as the attractant with the addition of 6% permethrin insecticide. These slow-release formulations (Last Call™; see U.S. Pat. No. 5,759,561), carried in a waterproof, UV absorbing gelatinous matrix, were applied to potato foliage via plastic containers with nozzles calibrated to deliver 50 μl droplets; other slow-release formulations can be used (see, for example, U.S. Pat. No. 5,707,638).

Field Plot Design: The work was conducted at the University of Maine's Rogers Farm in Stillwater, Me., U.S.A. The experimental area consisted of a 91.44 m×4.57 m foliated, previously untreated margin of a 0.404 Ha potato field (var. Kennebec). This area contained four blocks, each containing three treatment plots. The blocks were separated by a minimum of 3 m. Each plot measured 2.44 m×2 planted rows and was separated from plots within the same block by a minimum of two planted rows. The three treatment plots were arranged at random within each block, and one treatment was applied per plot.

Treatment Application: All plants within attractant or attracticide plots were treated with five 50 μl droplets per canopy level (1 m, 0.64 m, 0.32 m). The experiment was initiated (day 0) and densities of all CPB life stages were recorded prior to treatment ($N_o$ on FIGS. 2 and 3). Following this measurement, treatments were assigned to plots at random. Plots were sampled for densities of all CPB life stages every 24 hours for the next three days (days 1–3). Following the day 3 measurement, treatments were re-applied. As before, plots were sampled for densities of all CPB life stages every 24 hours for the next three days (days 4–6). Thus, there were a total of six sampling days following initiation of the experiment on day 0.

Sampling Regime: At the time of sample measurement, four plants per plot (two plants per row) were selected at random and the densities of all CPB life stages were recorded. Initial insect densities ($N_o$) were determined by sampling 48 plants, calculated as: (4 plants sampled/plot)×(3 plots)×(4 blocks). Experimental insect densities were determined by sampling 288 plants, calculated as: (4 plants sampled/plot)×(3 plots)×(4 blocks)×(6 sampling days).

Data Analysis: Repeated measures analysis of variance (ANOVA) was conducted using SAS PROC GLM on transformed data [x=ln (y+0.05)], and mean separation was conducted using the Student-Newman-Keuls Multiple Range Test (SAS Institute, 1987 SAS/STAT guide for personal computers, version 6 ed., SAS Institute, Cary, N.C.).

Figure 2:
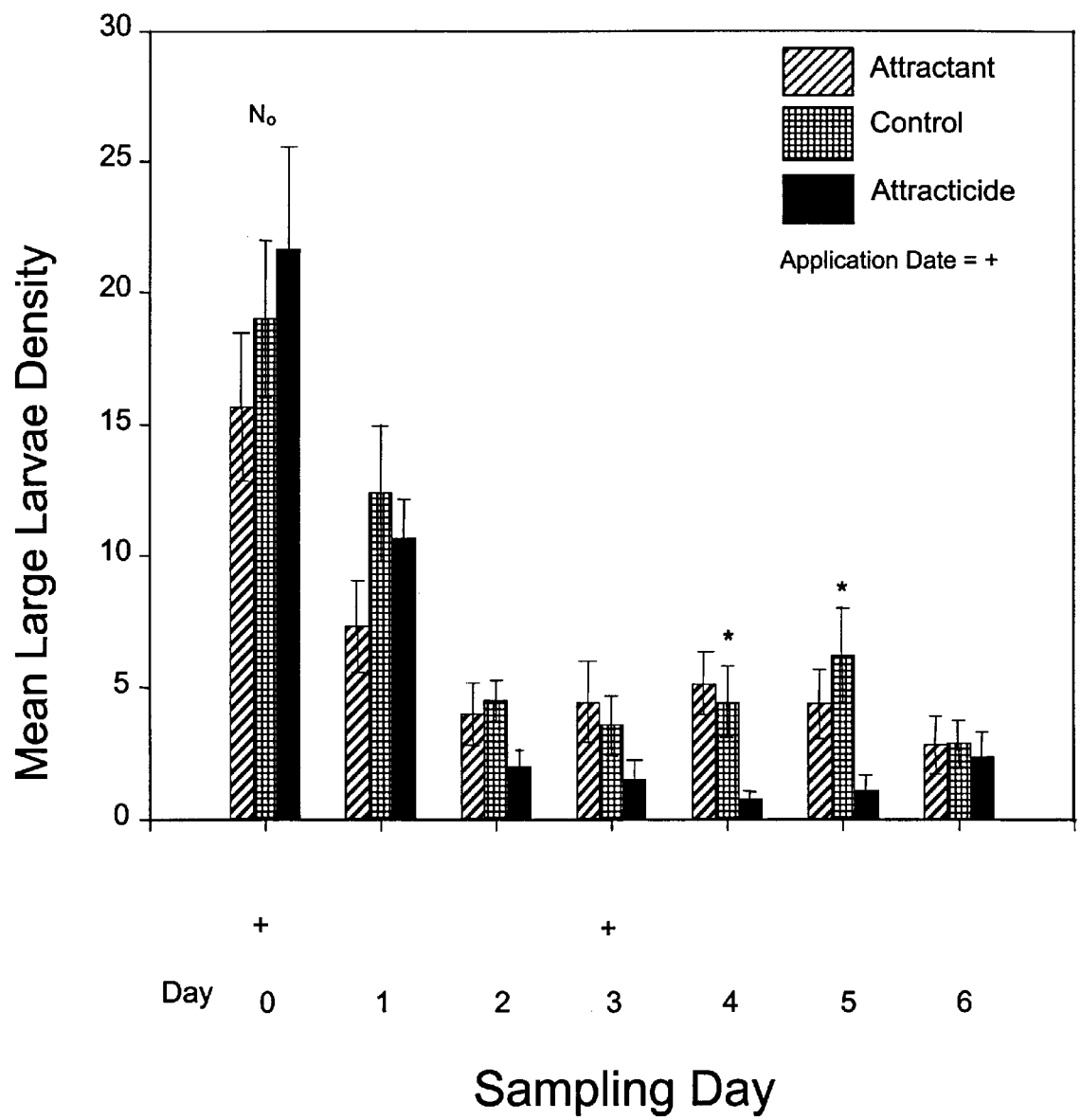
FIG. 2 shows the mean number of Colorado potato bettle larve ($3^{rd}$ and $4^{th}$ instars) (per treatment of plants by sampling date (±1SE)
Figure 3:
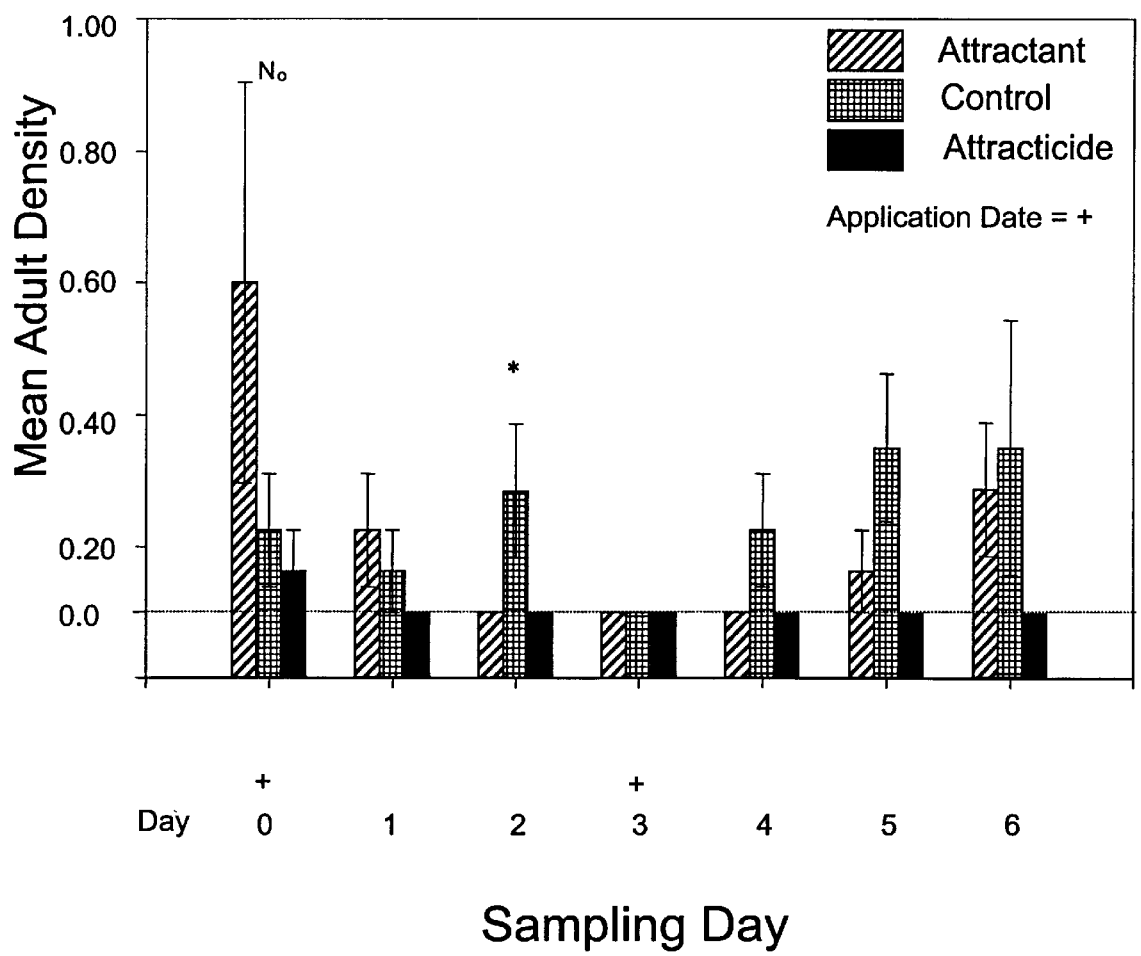
FIG. 3 shows mean number of Colorado potato beetle adults per treatment of plants by sampling date (±1SE).

Results: Overall mean densities of both adults (p=0.0082) and large larvae ($3^{rd}$ and $4^{th}$ instars; p=0.0399) in attracticide plots were significantly lower than in both attractant and control plots (Table 1). However, there were no significant differences in overall mean CPB densities by treatment for small larvae ($1^{st}$ and $2^{nd}$ instars) and egg masses (p>0.05; Table 1). Despite the fact that overall mean densities of adult and large larvae in attracticide plots were significantly lower than in both attractant and control plots, daily mean densities were only significantly different on certain days within the six day sampling period. Daily mean densities for large larvae in attracticide plots were significantly less than that of control and attractant plots on sampling days four (p=0.003) and five (p=0.002) of six days (FIG. 2). Overall daily large larvae densities were less than that for control plots on all six sampling days (days 1–6) and less than that for attractant plots on five of six sampling days (days 2–6) (FIG. 2). Although adult initial mean density (N.) was lowest in attracticide plots when the experiment was initiated on day 0, mean density for this treatment dropped to zero on day one and remained there for the duration of the experiment (FIG. 3). Adult daily mean densities in attracticide plots were significantly less than that of control and attractant plots on sampling day two (p=0.039). Overall daily adult densities in attracticide plots were less than that of control plots on day 0 ($N_o$) and on five of six sampling days (days 1–2 and days 4–6). Overall daily adult densities in attracticide plots were less than that of attractant plots on day 0 ($N_o$) and for three of six sampling days (days 1, 5 and 6).

Discussion: Given the experimental results above, the attracticide formulation shows promise as a tool for integrated CPB management. For both adults and large larvae, there were significantly fewer total individuals in attracticide plots than in the other treatment plots (Table 1). With the exception of day one, attracticide plots contained the least amount of large larvae on all sampling days (days 2–6) following initiation of the experiment, with days four and five containing significantly less than the other treatment plots (FIG. 2). Given that large larvae initial mean daily density ($N_o$) prior to treatment application on day 0 was highest in attracticide plots, this result suggests that plant volatile-based control measures may be particularly promising with regard to larval-stage CPB management.

Despite the fact that adult initial mean daily density ($N_o$) prior to initiation of the experiment was lowest in attracticide plots, no adults were found in attracticide plots following initiation of the experiment (FIG. 3). Although there were no significant differences in total mean CPB density by treatment for small larvae and egg masses, there were fewer of each life stage in attracticide plots than in attractant and control plots (Table 1). This particular result may have been confounded by the fact that small larvae and egg mass densities are generally in decline at this point in the Maine growing season, thereby making resolution of potential treatment differences difficult.

Plant attractant-based technologies may help reduce grower reliance on large-scale insecticide applications while maintaining acceptable levels of production. A potential field deployment strategy includes the use of plant attractants to facilitate CPB aggregation in border regions of production areas. Without being bound by theory, a chemical attractant applied to plants in the field perimeter would draw the pestiferous population away from the core of the production area. In an effort to reduce chemical input into the system, only these border regions would be treated with an insecticidal agent.

The greater purposes of plant chemistry-based management strategies are to effectively manage pest populations with reduced input of toxic chemicals, and to increase overall environmental quality of production areas. The efficacy of the attracticide strategy is likely to increase when incorporated into an integrated management program. Therefore, the results of this preliminary study suggest that host volatile-based strategies hold promise as integrated pest management tools for environmentally-sound management of Colorado potato beetle.

All of the references cited herein are incorporated by reference in their entirety. The following U.S. Patents are also incorporated by reference in their entirety: U.S. Pat. Nos. 5,759,561; 5,707,638; 5,648,390; 5,607,670; 5,468,770; 5,290,556; 5,273,996. Also incorporated by reference in their entirety are Pickett, J. A., et al., Agriculture Ecosystems & Environment, 64: 149–156 (1997), Behavior-modifying chemicals for insect management: applications of pheromones and other attractants, Richard L. Ridgway, Robert M. Silverstein, May N. Inscoe (eds.), 1990, Marcel Dekker, Inc., New York, N.Y.; Dickens, J. C., Agr. For. Ent., 2(3): 167–172 (2000); Dickens, J. C., Behavioral response of larvae of the Colorado potato beetle, (*Leptinotarsa decemlineata* Say (Coleoptera: Chrysomelidae) to host plant volatile blends attractive to adults, Agr. For. Ent., In press.

Thus, in view of the above, the present invention concerns (in part) the following:

A composition (with or without an insecticide) for attracting Colorado potato beetles, comprising or consisting essentially of or consisting of a carrier material and a Colorado potato beetle attracting effective amount of
(a) (Z)-3-hexenyl acetate, (±)-linalool, nonanal, and methyl salicylate (VII), or
(b) (Z)-3-hexenyl acetate, (±)-linalool, and methyl salicylate (VIII), or
(c) (Z)-3-hexen-1-ol, (E)-2-hexen-1-ol, and (±)-linalool (X), or
(d) (Z)-3-hexenyl acetate and methyl salicylate (XI), or
(e) (Z)-3-hexenyl acetate and (±)-linalool (XII).

The above composition further containing an insecticide.

A method for attracting Colorado potato beetles to an object or area, comprising treating the object or area with a Colorado potato beetle attracting composition (with or without an insecticide) comprising or consisting essentially of or consisting of a carrier material and a Colorado potato beetle attracting effective amount of (a) (Z)-3-hexenyl acetate, (±)-linalool, nonanal, and methyl salicylate (VII), or (b) (Z)-3-hexenyl acetate, (±)-linalool, and methyl salicylate (VIII), and wherein said beetles are larvae or adults, or (c) (Z)-3-hexen-1-ol, (E)-2-hexen-1-ol, and (±)-linalool (X), or (d) (Z)-3-hexenyl acetate and methyl salicylate (XI), or (e) (Z)-3-hexenyl acetate and (±)-linalool (XII).

The attractants of the present invention exclude the five component blend containing (Z)-3-hexen-1-ol, (E)-2-hexen-1-ol, (±)-linalool, nonanal, and methyl salicylate.

A composition (with or without an insecticide) for repelling Colorado potato beetles, comprising or consisting essentially of or consisting of a carrier material and a Colorado potato beetle repelling effective amount of (Z)-3-hexen-1-ol, (E)-2-hexen-1-ol, (±)-linalool, nonanal, salicylate, and β-caryophyllene (I or II).

A method for repelling Colorado potato beetles from an object or area, comprising treating the object or area with a Colorado potato beetle repelling composition (with or without an insecticide) comprising or consisting essentially of or consisting of a carrier material and a Colorado potato beetle repelling effective amount of (Z)-3-hexen-1-ol, (E)-2-hexen-1-ol, (±)-, linalool nonanal, methyl salicylate, and β-caryophyllene (I or II).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Source and purity of chemicals used in behavioral tests.

| Chemical | Purity (%) | Source[1] |
|---|---|---|
| Green leaf volatiles | | |
| (Z)-3-hexenol | 98 | A |
| (E)-2-hexenol | 97 | A |
| (Z)-3-hexenyl acetate | 98 | B |
| Aliphatic aldehyde | | |
| nonanal | 95 | A |
| Monoterpene | | |
| (+)-linalool | 97 | A |
| Sesquiterpene | | |
| β-caryophyllene | 99 | C |
| Benzenoid | | |
| methyl salicylate | 99 | A |

[1]A-Aldrich Chemical Co., P.O. Box 14508, St Louis, MO, USA; B-Sigma Chemical Co.,; C-ICN Biomedicals Inc., 1263 South Chillicotte Rd., Aurora, IL

TABLE 2

Behavioral responses of the Colorado potato beetle to volatiles emitted by mechanically-damaged foliage of potato or tomato plants (T) versus control (C), and mechanically-damaged potato foliage versus mechanically-damaged tomato or soybean foliage. Asterisks indicate that response to blend differs from control or other paired treatment (*-P < 0.05; **-P < 0.01) by testing the hypothesis that the binomial proportion is significantly different from p = 50% using the standard normal approximation (Brase & Brase, 1983).

| Orientation of Colorado potato beetle | A. MD[1] potato vs. B. control | A. MD tomato vs. B. control | A. MD potato vs. B. MD tomato | A. MD potato vs. B. MD soybean |
|---|---|---|---|---|
| #[2]A:#B | 50:30 | 23:17 | 23:17 | 28:12 |
| % ± S.E. response to A | 62.5 ± 10.7* | 57.5 ± 7.8 | 57.5 ± 7.8 | 70 ± 7.2** |

[1]4.8 g mechanically-damaged foliage
[2]# = number of insects attracted to this side of the olfactometer

TABLE 3

Behavioral responses of the Colorado potato beetle to individual compounds and synthetic blends of volatiles emitted by potato plants (T) versus control (C). Asterisks indicate that response to blend differs from control (*P < 0.05; **P < 0.01) by testing the hypothesis that the binomial proportion is significantly different from p = 50% using the standard normal approximation (Brase & Brase, 1983). "+" indicates presence of chemical in blend.

| Chemical | I | II | III | IV | V |
|---|---|---|---|---|---|
| (Z)-3-hexen-1-ol | | | +low | + | + |
| (E)-2-hexen-1-ol | | | +low | + | + |
| (Z)-3-hexenyl acetate | | | + | + | |
| (±)-linalool | | | + | + | + |
| nonanal | | | + | + | + |
| methyl salicylate | | | + | + | + |
| β-caryophyllene | | | +low | | |
| #[1]T:#C % ± S.E response to T | | | 22:18 55 ± 7.9 | 17:23 42.5 ± 7.8 | 18:22 45 ± 7.9 |

TABLE 3-continued

Behavioral responses of the Colorado potato beetle to individual compounds and synthetic blends of volatiles emitted by potato plants (T) versus control (C). Asterisks indicate that response to blend differs from control (*$P < 0.05$; **$P < 0.01$) by testing the hypothesis that the binomial proportion is significantly different from p = 50% using the standard normal approximation (Brase & Brase, 1983). "+" indicates presence of chemical in blend.

| Chemical | VI | VII | VIII | IX | X | XI |
|---|---|---|---|---|---|---|
| (Z)-3-hexen-1-ol | +low | | | | +low | |
| (E)-2-hexen-1-ol | +low | | | | +low | |
| (Z)-3-hexenyl acetate | | + | + | | | + |
| (±)-linalool | + | + | + | + | + | |
| nonanal | + | + | | + | | |
| methyl salicylate | + | + | + | + | | + |
| β-caryophyllene | | | | | | |
| #T:#C % ± S.E. response to T | 43:17 71.7 ± 7.1** | 66:16 80.5 ± 4.4** | M - 38:2 95 ± 3.4** F - 20:20 50 ± 7.9 | 19:21 47.5 ± 7.9 | 32:8 80.0** | 28:12 70 + 7.2** |

| Chemical | XII | XIII | XIV | XV | XVI |
|---|---|---|---|---|---|
| (Z)-3-hexen-1-ol | | | | | |
| (E)-2-hexen-1-ol | | | | | |
| (Z)-3-hexenyl acetate | + | | + | | |
| (±)-linalool | + | + | | + | |
| nonanal | | | | | |
| methyl salicylate | | + | | | + |
| β-caryophyllene | | | | | |
| #T:#C % ± S.E. response to T | 34:6 85 ± 5.6** | 22:18 55 ± 7.9 | 16:24 40 ± 7.7 | 20:20 50 ± 7.9 | 20:20 50 ± 7.9 |

[1]# = number of insects attracted to this side of the olfactometer

TABLE 4

Behavioral responses of the Colorado potato beetle to synthetic blends of volatiles emitted by potato plants versus volatiles emitted by the foliage of mechanically-damaged potato plants. Responses to paired treatments are not significantly different by testing the hypothesis that the binomial proportion is significantly different from p = 50% using the standard normal approximation (Brase & Brase, 1983).

| Orientation of Colorado potato beetle | A. VI vs. B. VII | A. MD[1] potato vs. B. VI | A. MD potato vs. B. VII |
|---|---|---|---|
| #[2]A:#B | 48:32 | 47:33 | 45:35 |
| % ± S.E. response to A | 60.0 ± 5.5 | 58.8 ± 5.5 | 56.3 ± 5.5 |

[1] 4.8 g mechanically-damaged foliage
[2] # = number of insects attracted to this side of the olfactometer

TABLE 5

Behavioral responses of second instar larvae of Colorado potato beetle to synthetic blends of volatiles emitted by potato plants (T) versus control (C). All blends were attractive to adult beetles. Asterisks indicate response to blend differs from control (* – P < 0.05) by testing the hypothesis that the binomial proportion is significantly different from p = 50% using the standard normal approximation (Brase & Brase, 1983). "+" indicates presence of chemical in blend.

| Chemical | VI | VII | VIII | X | XI | XII |
|---|---|---|---|---|---|---|
| (Z)-3-hexen-1-ol | + low | | | + low | | |
| (E)-2-hexen-1-ol | + low | | | + low | | |
| (Z)-3-hexenyl acetate | | + | + | | + | + |
| (±)-linalool | + | + | + | + | | + |
| nonanal | + | + | | | | |
| methyl salicylate | + | + | + | | + | |
| β-caryophyllene | | | | | | |
| #T:#C | 9:11 | 10:10 | 29:11 | 12:8 | 11:9 | 12:8 |
| % ± S.E. response to T | 45 ± 11.1 | 50 ± 11.2 | 72.5 ± 7.1* | 60 ± 11 | 55 ± 11.1 | 60+11 |

TABLE 6

Behavioral responses of fourth instar larvae of Colorado potato beetle to synthetic blends of volatiles emitted by potato plants (T) versus control (C). All blends were attractive to adult beetles. Asterisks indicate response to blend differs from control (* – P < 0.05) by testing the hypothesis that the binomial proportion is significantly different from p = 50% using the standard normal approximation (Brase & Brase, 1983). "+" indicates presence of chemical in blend.

| Chemical | VI | VII | VIII | X | XI | XII |
|---|---|---|---|---|---|---|
| (Z)-3-hexen-1-ol | + low | | | + low | | |
| (E)-2-hexen-1-ol | + low | | | + low | | |
| (Z)-3-hexenyl acetate | | + | + | | + | + |
| (±)-linalool | + | + | + | + | | + |
| nonanal | + | + | | | | |
| methyl salicylate | + | + | + | | + | |
| β-caryophyllene | | | | | | |
| #T:#C | 8:12 | 10:10 | 18:2 | 10:10 | 7:13 | 9:11 |
| % ± S.E. response to T | 40 ± 11 | 50 ± 11.2 | 90 ± 6.7* | 50 ± 11.2 | 35 ± 10.7 | 45 ± 11.1 |

We claim:

1. A method for attracting Colorado potato beetles to an object or area, comprising treating the object or area with a Colorado potato beetle attracting composition consisting essentially of a carrier material and a Colorado potato beetle attracting effective amount of
   (a) (Z)-3-hexenyl acetate, (±)-linalool, nonanal, and methyl salicylate,
   (b) (Z)-3-hexenyl acetate, (±)-linalool, and methyl salicylate,
   (c) (Z)-3-hexen-1-ol, (E)-2-hexen-1-ol, and (±)-linalool,
   (d) (Z)-3-hexenyl acetate and methyl salicylate, or
   (e) (Z)-3-hexenyl acetate and (±)-linalool.

2. The method according to claim 1, wherein said composition consists essentially of a carrier material and a Colorado potato beetle attracting effective amount of (Z)-3-hexenyl acetate, (±)-linalool, nonanal, and methyl salicylate.

3. The method according to claim 1, wherein said composition consists essentially of a carrier material and a Colorado potato beetle attracting effective amount of (Z)-3-hexenyl acetate, (±)-linalool, and methyl salicylate.

4. The method according to claim 1, wherein said composition consists essentially of a carrier material and a Colorado potato beetle attracting effective amount of (Z)-3-hexen-1-ol, (E)-2-hexen-1-ol, and (±)-linalool.

5. The method according to claim 1, wherein said composition consists essentially of a carrier material and a Colorado potato beetle attracting effective amount of (Z)-3-hexenyl acetate and methyl salicylate.

6. The method according to claim 1, wherein said composition consists essentially of a carrier material and a Colorado potato beetle attracting effective amount of (Z)-3-hexenyl acetate and (±)-linalool.

7. The method according to claim 1, wherein said beetles are larvae and said composition consists essentially of a carrier material and a Colorado potato beetle attracting effective amount of (Z)-3-hexenyl acetate, (±)-linalool, and methyl salicylate.

8. The method according to claim 1, wherein said beetles are adults.

* * * * *

UNITED STATES PATENT AND TRADEMARK OFFICE
CERTIFICATE OF CORRECTION

PATENT NO.      : 6,479,046 B2                                           Page 1 of 1
DATED           : November 12, 2002
INVENTOR(S)     : Joseph C. Dickens et al.

It is certified that error appears in the above-identified patent and that said Letters Patent is hereby corrected as shown below:

Title page,
Insert Item:
-- [73] Assignee: The United States of America, as represented by the Secretary of Agriculture, Washington, D.C. 20231 --.

Signed and Sealed this

Second Day of September, 2003

JAMES E. ROGAN
*Director of the United States Patent and Trademark Office*